US010667740B2

(12) United States Patent
Edgin et al.

(10) Patent No.: US 10,667,740 B2
(45) Date of Patent: Jun. 2, 2020

(54) SYSTEM AND METHODS FOR NEUROPSYCHOLOGICAL ASSESSMENT

(71) Applicant: The Arizona Board of Regents for and on behalf of the University of Arizona, Tucson, AZ (US)

(72) Inventors: Jamie Edgin, Tucson, AZ (US); Caron Clark, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 733 days.

(21) Appl. No.: 14/788,322

(22) Filed: Jun. 30, 2015

(65) Prior Publication Data

US 2015/0379877 A1    Dec. 31, 2015

Related U.S. Application Data

(60) Provisional application No. 62/019,216, filed on Jun. 30, 2014.

(51) Int. Cl.
*A61B 5/00*    (2006.01)
*G09B 1/06*    (2006.01)

(52) U.S. Cl.
CPC .............. *A61B 5/4088* (2013.01); *G09B 1/06* (2013.01)

(58) Field of Classification Search
CPC ........................................................ A61B 5/16
USPC ........................................................ 434/236
See application file for complete search history.

(56) References Cited

U.S. PATENT DOCUMENTS

2003/0180696 A1*  9/2003  Berger ................. G09B 17/003
                                                434/178

OTHER PUBLICATIONS

Wikipedia: Corsi block-tapping test, Web Archive, Web. Jul. 1, 2013. <https://web.archive.org/web/20130701000000*/https://en.wikipedia.org/wiki/Corsi_block-tapping_test>.*
Kessels RP, van den Berg E, Ruis C, and Brands AM, ("The backward span of the Corsi Block-Tapping Task and its association with the WAIS-III Digit Span. Assessment", 15(4): 426e434, 2008).*
Bucks, R. S., & Willison, J. R. (1997). Development and validation of the Location Learning Test (LLT): A test of visuo-spatial learning designed for use with older adults and in dementia. Clinical Neuropsychologist, 11, 273-286 (Year: 1997).*

* cited by examiner

*Primary Examiner* — Thomas J Hong
(74) *Attorney, Agent, or Firm* — Larson & Anderson, LLC (57) ABSTRACT

A hiding board includes a flat surface; and a plurality of containers arranged in a random fashion on the flat surface and secured thereto, each container being configured to receive a three-dimensional object from a user. A method for neuropsychological assessment includes presenting one or more three-dimensional objects to a participant in a first arrangement on a hiding board; removing the one or more three-dimensional objects from the hiding board; re-presenting the one or more three-dimensional objects to the participant in an arrangement that is different from the first arrangement; and tasking the participant with recreating the first arrangement.

9 Claims, 8 Drawing Sheets

SYSTEM AND METHODS FOR NEUROPSYCHOLOGICAL ASSESSMENT

CROSS-REFERENCE TO RELATED APPLICATION

This application claims the benefit of U.S. Provisional Patent Application No. 62/019,216, filed Jun. 30, 2014, which is hereby incorporated by reference in its entirety.

BACKGROUND OF THE INVENTION

This application relates to a system and methods for neuropsychological assessment and, more specifically, the assessment of memory and learning functions, including verbal associative memory, working, and prospective memory and executive functions.

Neuropsychological assessments, including memory performance assessments, are designed to assess cognitive ability and are widely used in educational program planning, clinical assessment, and drug efficacy (clinical) trials. Many neuropsychological assessments, however, assume a minimum level of cognitive function or knowledge that is not met by all populations. As a result, many neuropsychological assessments are not suitable for young children (under the age of 5) or individuals with cognitive delay or cognitive impairment. Populations such as these present significant challenges in the context of neuropsychological assessments because existing assessments are often too difficult and/or do not cater for varying levels of attention, language, and/or motor proficiency.

Memory is central to effective learning and everyday function. Impairments in memory also form a pervasive part of many neuropsychological and genetic disorders. Valid, developmentally appropriate, and sensitive measures of memory performance permit the creation of a clinical profile that characterizes different facets of a participant's memory. The clinical profile may help to determine the type and degree of cognitive or memory impairment, monitor progression of a disorder or improvement or decline in cognitive or memory function over time, provide feedback regarding the most effective ways to present information to an individual, or be used to evaluate the effectiveness of educational remediation, or pharmacological or surgical treatment. For example, some pharmacological treatments for Down syndrome (DS), autism, and Fragile X syndrome act on brain regions of known importance for memory and learning, including the hippocampus, medial-temporal lobes, and prefrontal cortex. Changes in memory assessment performance over time can indicate whether a pharmacological treatment is effective for an individual. This type of feedback is critical to the development of new treatments, clinical trials, and individual treatment plans.

Currently, there are no measures of memory and learning standardized for use with children under the age of 5 years that are comprehensive in their scope, covering the assessment of memory for single items, space, and episodic learning. While measures exist for older populations, those measures are not necessarily appropriate for populations having cognitive delays and/or impairments. Further, no single available test includes optimal cognitive measures to cover the profile of lifespan cognitive development when there is cognitive impairment and age-related decline, such as is in individuals with DS. Finally, memory performance assessments used with typically-developing, adult populations are often unsuitable for use with populations having cognitive impairment, including memory disorders such as Alzheimer's disease or dementia. Thus, there exists a need for a comprehensive memory assessment suitable for across the lifespan and in different populations, including young children and individuals with cognitive delay or impairment.

SUMMARY OF THE INVENTION

The present invention provides a system for memory assessment that includes a plurality of three-dimensional objects selected to be both recognizable and identifiable by a participant, and a plurality of containers arranged randomly on and affixed to a flat surface. Each of the plurality of containers is configured to receive one of the plurality of three-dimensional objects and has translucent sides. When viewed from above, each container forms an area of contrast with the flat surface. This provides a three-dimensional tool for memory assessment that is appropriate for a variety of populations, including young children and those with cognitive impairments. This tool, along with other newly designed record forms, allows for the unique assessment of different memory processes in a child-friendly manner.

The present invention also provides for a variety of memory assessments suitable for use with young children and individuals with cognitive impairment and designed to measure verbal and visuospatial pattern recall and recognition, dependent on the medial temporal neural regions, and executive functions, dependent on the prefrontal cortex. The various memory assessments can be administered in various combinations and supplemented by other methods of memory assessment to provide a comprehensive assessment that includes the cognitive measures required to cover the profile of lifespan cognitive development when there is cognitive impairment. This comprehensive assessment includes assessments of verbal list learning, object recognition, scene recognition, spatial location memory, item in context memory, spatial working memory, verbal working memory, processing speed and controlled attention, and prospective memory.

DETAILED DESCRIPTION

It is well-established that memory is not a unitary construct, but rather a collection of short-term and long-term cognitive processes that allow for the storage and retrieval of information. Thus, it is desirable to consider different modalities of memory in assessing memory performance.

These modalities include recognition and recollection components of memory, which are modulated by distinct areas of the medial-temporal lobes, and flexible, goal-directed regulation of cognition and behavior, modulated by prefrontal-parietal neural circuits.

Figure 1:
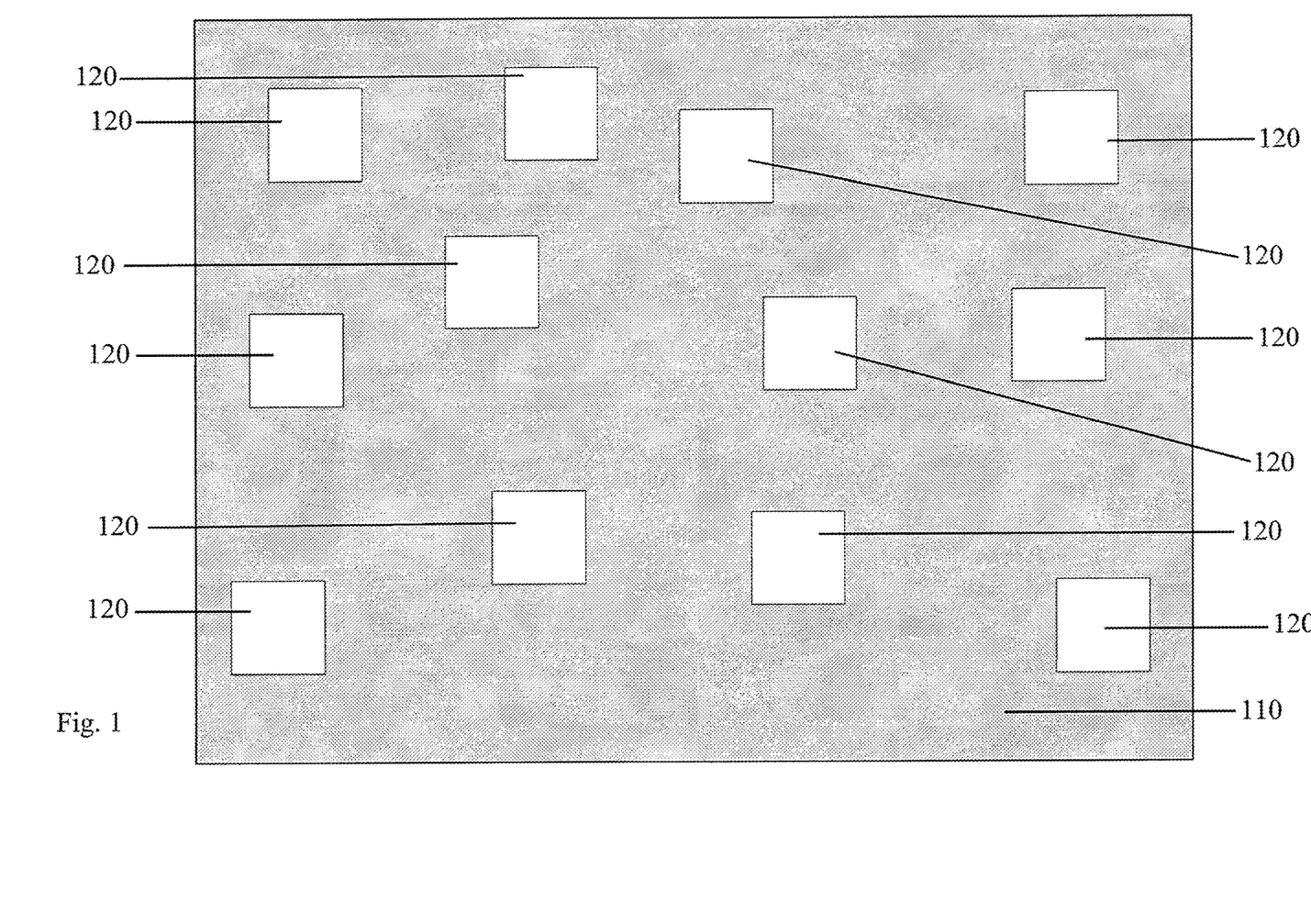
FIG. 1 illustrates a top view of a memory testing apparatus in accordance with the present invention.
Figure 2:
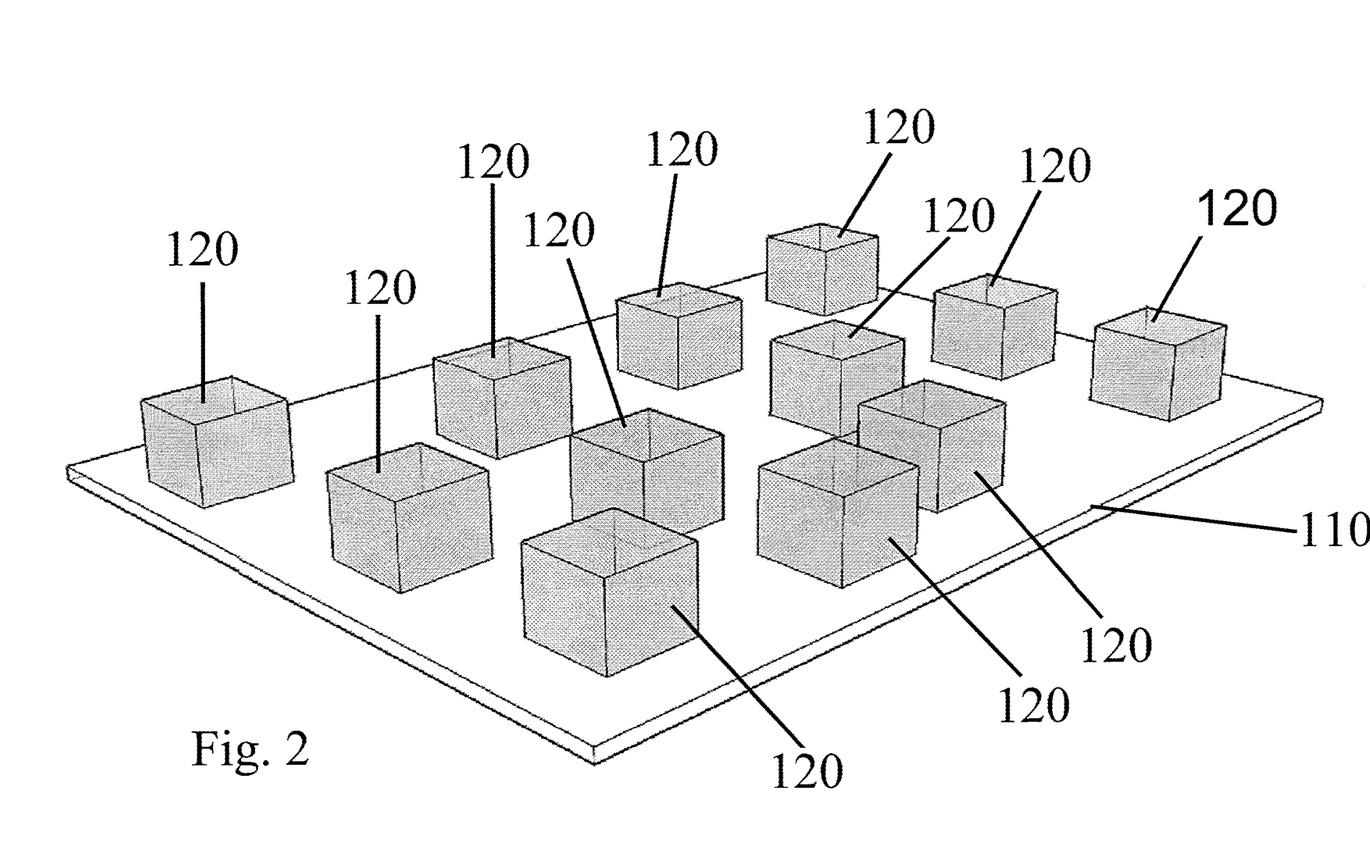
FIG. 2 illustrates a perspective view of a memory testing apparatus in accordance with the present invention.
Figure 3:
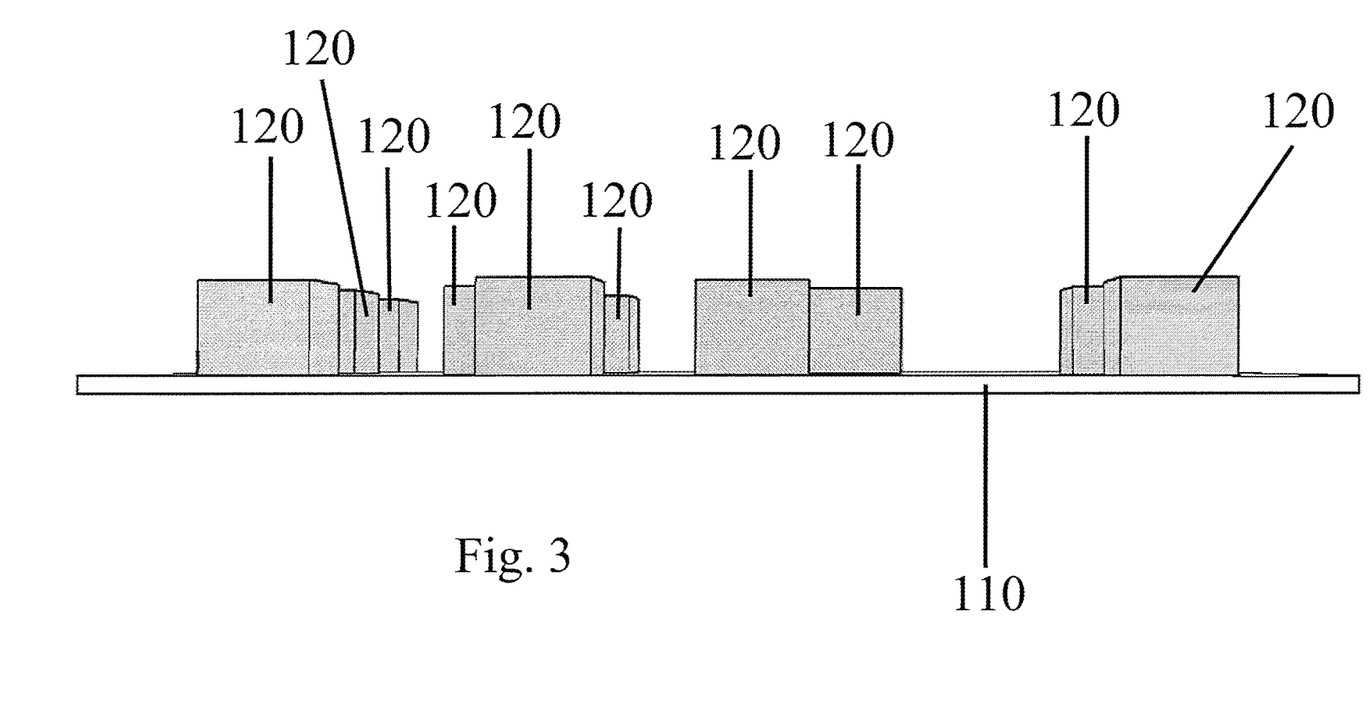
FIG. 3 illustrates a side view of a memory testing apparatus in accordance with the present invention.

An exemplary memory testing apparatus for use with the assessments in accordance with the present invention is illustrated in FIGS. 1-3. In the context of the assessments described herein, this memory testing apparatus may be referred to as a "hiding board." The hiding board illustrated in FIGS. 1-3 includes a flat surface (or mounting surface) 110 and a number of containers 120. Containers 120 are arranged in a random arrangement on the flat surface 110. Preferably, the containers are detachably or permanently secured to the flat surface. While the exemplary hiding board illustrated in FIGS. 1-3 includes 12 containers, it should be appreciated that the number of containers may be varied without departing from the scope of the invention. Further, in some implementations, the hiding board may be implemented using a computing device or digital representation.

Preferably, the containers 120 are of the same size, and the size is sufficient to receive one or more three-dimensional objects used in one or more assessments in accordance with the present invention. However, the sizes of the containers may vary. The containers 120 illustrated in FIGS. 1-3 are preferably transparent, so that three-dimensional objects placed into the containers are visible when viewed from the side or at an angle. However, it should be appreciated that the containers may be translucent or of any color. In some implementations, the bottom of each container 120 may be of a color that provides visual contrast against the flat surface 110. For example, if the flat surface 110 is a dark color, preferably black, the bottoms of the containers 120 are preferably white. It is preferable that the containers 120 are identical in appearance, but the containers may vary in appearance without departing from the scope of the invention. Preferably, each container is labeled with an index marker (letter, number, etc.) for identification of the container by the test administrator.

The flat surface 110 may be a tray or board designed for portability, for example having dimensions of approximately 12" by 16", so that it can be easily transported and removed from the participant's field of view during administration of the assessments presented herein. The exact dimensions of the flat surface, however, are not critical to the assessment and may vary without departing from the scope of the invention. The flat surface may be of any thickness sufficient to support the plurality of containers. In some implementations, the flat surface may be a table, desk, or shelf, and the test participant may be moved to and from the flat surface instead of moving the flat surface to and from the test participant. In this context, flooring may be used to create a background for the hiding board. In this implementation or in the portable implementation, a cloth having a cutout of sufficient size to expose at least all of the containers, and preferably all of the containers surrounded by a border of visible flat surface, may be used to quickly and easily change the background colors/patterns. In some implementations, the flat surface 110 may be formed by a display device, such as a capacitive touch sensing screen or pressure sensitive screen to facilitate changing the background visible beneath and around the containers of the hiding board.

As illustrated in FIGS. 1-3, the containers are affixed to the flat surface in a random array. The random array is nonlinear and non-symmetric on the flat surface. This random arrangement makes it more difficult for a participant to influence the results of an assessment by using the arrangement of the containers to devise a spatial strategy. While one random arrangement of containers is illustrated in FIGS. 1-3, it should be appreciated that other random, nonlinear, non-symmetric, non-patterned arrangements of containers may be used.

The color or pattern presented on the flat surface of the hiding board may be varied or altered, or the hiding board may be placed on different backgrounds or affixed with borders or surface markers to change the cues, and thus the context, of the hiding board. For example, the hiding board may be placed on a bright, solid-colored background, such as an orange background. Alternatively, the hiding board may be placed on a patterned background, such as a blue and white chevron background. It should be understood that different background colors and patterns may be used to alter the context of the hiding board. This is particularly important because it allows for the assessment of memory for spatial configurations in different contexts.

The hiding board is used in conjunction with any of a variety of three-dimensional objects that at least partially fit within the containers of the AMAP board. Exemplary three-dimensional objects include, but are not limited to: a ring, a bug, a cup, a bow, a car, a heart, a duck, a bell, a flower, money (a coin), an egg, a small plastic tree, a key, a fish, an apple, a star, a plane, a hat, a bear, a ball, a spoon, a cake, a sock, and a balloon. However, any assortment of objects could be used, including recognizable objects and nameable and unnamable three-dimensional abstract shapes. It should be appreciated, however, that the number of three-dimensional objects used in the various methods described herein is not limited to twelve, nor are the three dimensional objects limited to those exemplary items described above. Any three-dimensional objects that fit at least partially within the containers of the hiding board may be used with the hiding board and in the assessments described herein. Preferably, the three-dimensional objects are selected so that the names for the objects are part of a young child's vocabulary, based on language norms, but in more difficult versions for older children the objects may be abstract. Additionally, the three-dimensional objects should be selected so that they are sized to fit within the containers of the hiding board while still being large enough for a participant, including a young child or an individual with motor impairment, to touch, grasp, and move throughout the various assessments disclosed herein. It is preferable that the objects also be selected to be sufficiently durable to withstand use over the course of repeated assessments. It may also be preferable to select three-dimensional objects that are likely to be appealing or of interest to the intended participant.

Together, the hiding board and the plurality of three-dimensional objects disclosed herein form a system for use in performing an assessment of memory and learning. The system may also include one or more other items including but not limited to figurines (including animal figures), one or more stimulus booklets presenting a variety of two-dimensional visual stimuli, small toys including but not limited to jacks, one or more "scene cards" depicting color or black and white images (including, but not limited to, outdoor scenes), one or more printed worksheets for use by the participant, one or more items intended to create marks on said worksheets, such as a stamp, marker, crayon, writing implement or the like, and a timing device such as a watch or stopwatch. Further, the system may include instructions for administering one or more memory assessments, and/or instructions for scoring those assessments. Instructions may be presented in any of a variety of manners including in writing, verbally, via audio or video recording, via computer, etc.

Figure 4:
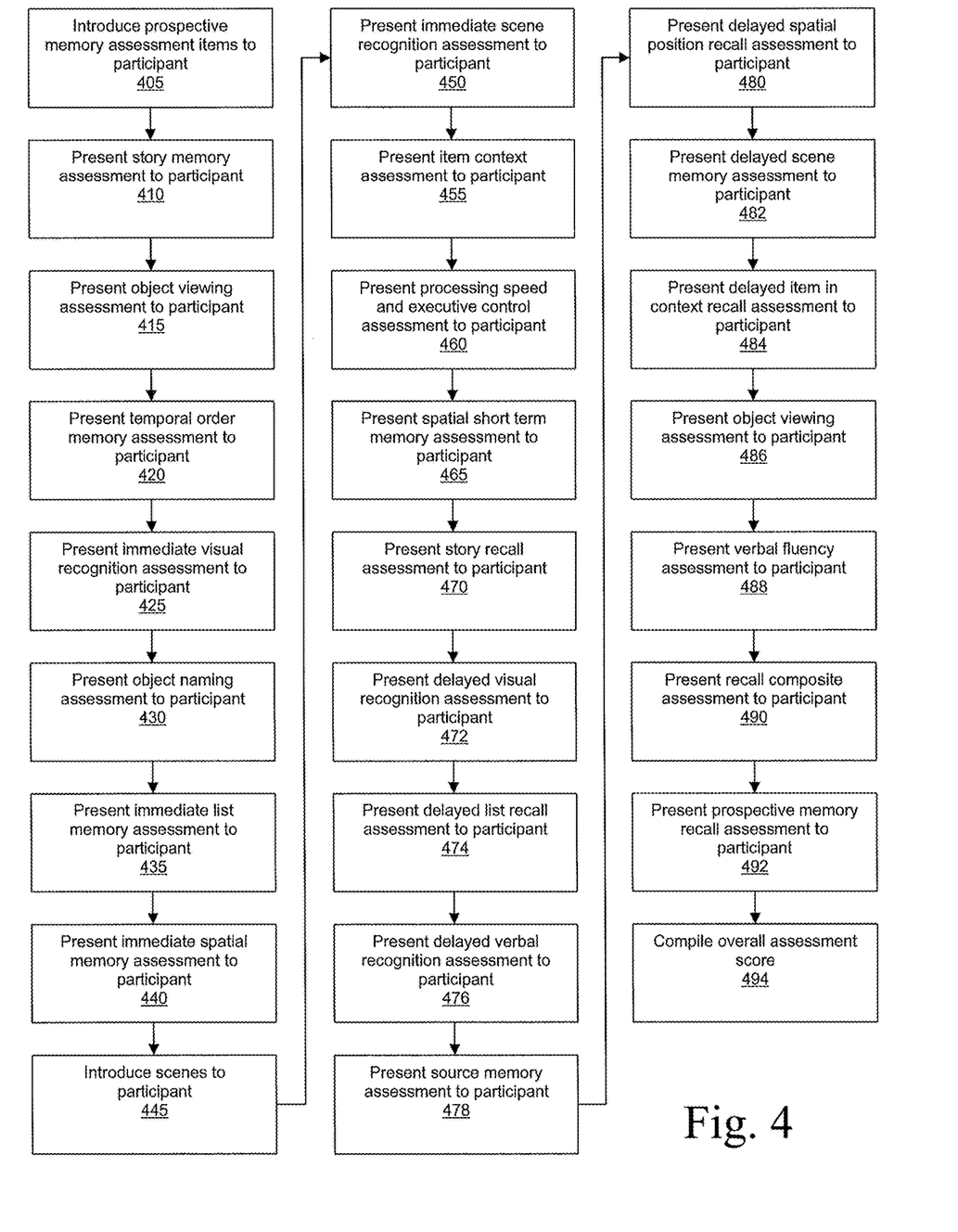
FIG. 4 illustrates an exemplary comprehensive assessment method in accordance with the present invention.

FIG. 4 illustrates an exemplary comprehensive assessment in accordance with the present invention. It should be understood that phases of the comprehensive memory assessment may be adapted if a participant is unable to complete one or more phases of the comprehensive memory assessment. This reduces the participant's frustration if the participant is unable to complete one or more phases of the comprehensive memory assessment, so that the inability to complete one phase has a minimal impact on the participant's ability to complete other phases of the comprehensive memory assessment. Further, it should be appreciated that the various portions of the comprehensive assessment disclosed herein may be administered individually as "short form" tests designed to assess individual aspects of memory, in various combinations with other portions of the comprehensive memory assessment disclosed herein to assess multiple aspects of memory, or in combination with established methods for memory assessment to create a multi-faceted profile of a participant's (or test subject's) memory.

In the context of the assessments described herein, it should be appreciated that various factors, such as the number of three-dimensional objects presented to the participant, the number of three-dimensional objects placed on the hiding board, the number of three-dimensional objects chosen by the test administrator, the length of times noted in the exemplary embodiments, and the like are for illustrative purposes only, and may be altered without departing from the scope of the invention. Further, the number of "trials" or number of times a particular assessment is performed is also presented for exemplary purposes, and is non-limiting. The number of trials may be varied. Further, if a participant is unable to complete a task after repeated attempts, many of the methods provided herein also include a "discontinue rule" intended to minimize frustration on the part of the participant, so that inability to perform one assessment is not detrimental to the remaining assessments. It should also be appreciated that each individual assessment administered herein should be scored, preferably upon administration of the assessment.

In neuropsychological assessments, the hiding board is used by presenting one or more three-dimensional objects to the participant in an arrangement on the hiding board; removing the one or more three-dimensional objects from the hiding board; re-presenting the one or more three-dimensional objects to the participant in a different arrangement, for example, on a tray; and tasking the participant with recreating the originally presented arrangement. The one or more three-dimensional objects may be identical, may vary in one or more physical characteristics, or may be unique objects. The arrangement may be an arrangement of a plurality of three-dimensional objects on the hiding board, or may be one or more three-dimensional objects that are moved from a first position to a second and/or subsequent position by a test administrator. The context of the hiding board may also be varied.

As illustrated in FIG. 4, an exemplary comprehensive assessment method disclosed herein begins by introducing one or more objects for prospective memory assessment in step 405. However, it should be appreciated that the prospective memory introduction may occur at any time during the comprehensive assessment, as long as sufficient time will pass between introduction of the item(s) and assessment of prospective memory recall to assess prospective memory. In step 410, the participant's story memory is assessed by reading a story to the participant, and then asking the participant to recall the story. The story memory assessment is scored by awarding points for verbatim recall of specific words, and recording variations or intrusions.

In step 415, an object viewing assessment is administered to the participant. In an exemplary object viewing assessment, multiple three-dimensional objects are presented to the participant, one at a time, and then the participant is asked to identify which object was presented in a specific order, such as which object was presented first. This may be repeated with different sets of objects. The object viewing assessment is scored by awarding points for correct identification of objects.

In step 420, a temporal order memory assessment is administered to a participant. In an exemplary temporal order memory assessment, a series of three dimensional objects is presented to the participant without naming the objects. Preferably, the participant touches each object. Subsets of this series of three dimensional objects are then presented to the participant at the same time, and the participant is instructed to identify which of the objects was presented first (or at a specific point) in the series. Preferably, multiple subsets of the series of objects is presented to the participant. Scoring is based on correct identification of objects.

In step 425, an immediate visual recognition assessment is administered to the user. In an exemplary immediate visual recognition assessment, this assessment is based on the series of three dimensional objects presented in the temporal order memory assessment. The participant is presented with multiple visual stimuli (preferably in the form of pictures, either reproduced on paper or in a test booklet, or presented via a computing device), and asked to identify which of those stimuli the participant saw in the temporal order memory assessment. Preferably, multiple groupings of stimuli are presented to the user, and the assessment is scored by awarding points for each correctly chosen stimulus.

In step 430, an object naming assessment is administered to the participant. In an exemplary object naming assessment, objects are presented to the participant one at a time, and the participant is asked to name the objects as they are presented. Scoring is based on correct identification of the objects.

In step 435, a present immediate list memory assessment is administered to the participant. In an exemplary immediate list memory assessment, the objects from the object naming assessment are removed from sight, and the participant is asked to identify all of the items that were presented in the object naming assessment. Multiple trials may be administered. Scoring is based on participant responses. Preferably credit is given if a participant consistently substitutes words (for example, if the participant identifies a "bug" as a "beetle" or an "ant").

In step 440, an immediate spatial memory assessment is administered to the participant. In an exemplary implementation, the immediate spatial memory assessment utilizes the hiding board described therein, and a plurality of identical or similar three dimensional objects, such as jacks. The objects are placed in containers on the hiding board, and the participant is provided with an opportunity to view the placement of the items on the hiding board. The objects are then removed from the hiding board, and then the participant is tasked with placing the objects in their original locations on the hiding board. This process may be repeated for multiple trials. Scoring awards points for each item correctly placed on the hiding board. Preferably, the task is discontinued if the participant correctly places three or fewer of the objects over three trials (remaining trials are scored as zero). If the participant correctly places all items in two consecutive trials, trials may be discontinued and any remaining trials should be awarded full credit/points.

In step 445, visual stimuli are administered to the participant. In an exemplary implementation, scene cards (or the electronic equivalent, for example, pictures presented on a computing device) are individually presented to the participant for a predetermined period of time.

In step 450, an immediate scene recognition assessment is administered to the participant, based on the visual stimuli presented in step 445. In an exemplary implementation, the scene cards (or equivalent) are removed from the participant's sight. Multiple scenes are then presented to the participant (either via a stimuli booklet or the electronic equivalent, for example, by displaying multiple images via a computing device), and the participant is asked to identify which of the images the participant saw in step 445. Preferably, this is repeated for each of the images or scenes presented to the participant in step 445. Scoring awards points for each correctly identified image.

In step 455, an item context recognition assessment is administered to the participant. In an exemplary item context recognition assessment, a plurality of objects (for example, 9 three dimensional objects) are arranged in containers on a hiding board that has been placed on a patterned background (referred to herein as context), such as a blue and white chevron mat, or where the appearance of the flat surface of the hiding board has been altered. The participant is invited to view the objects on the hiding board while the hiding board is on the patterned background. The objects are then removed from the hiding board and placed on a tray. The tray of items is presented to the participant, and the participant is asked to place each object into its original location on the hiding board. If the items are not placed correctly on the hiding board, the test administrator moves the items to the correct location, and then the process is repeated. Preferably, 5 trials are completed. However, if a participant makes fewer than 3 correct placements on each of the first three trials, the task should be discontinued and all remaining trials should be scored as zero. If the participant correctly completes 2 consecutive trials, the task should be discontinued and all remaining trials awarded full credit. Otherwise, scoring awards points for each item correctly placed on the hiding board. In some implementations, the background may be changed to a solid color background or a differently patterned background, and the process is repeated.

Figure 6:
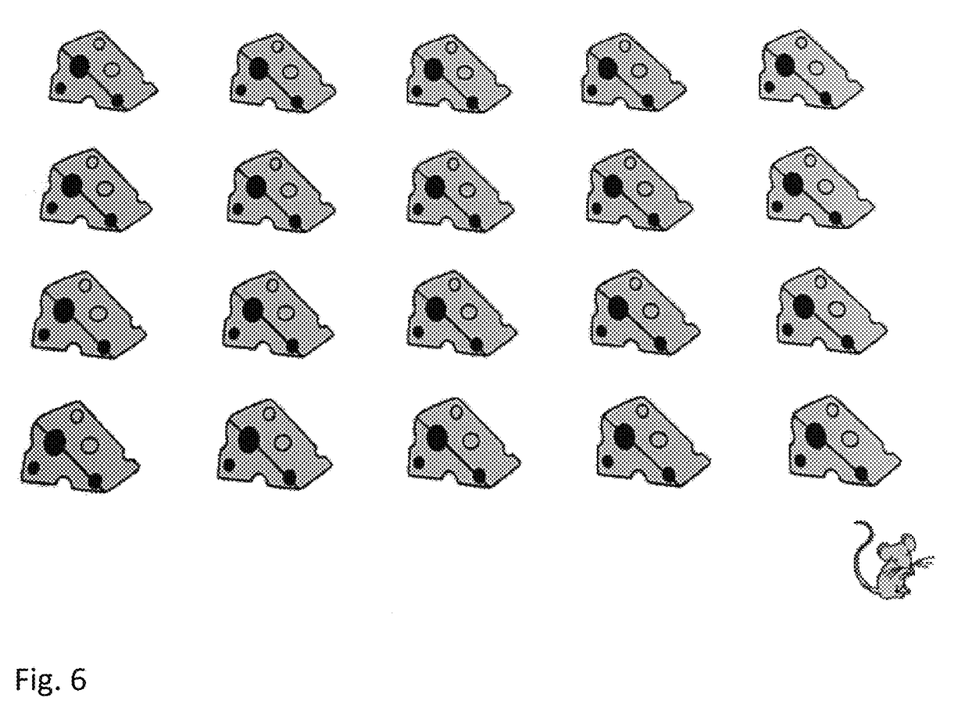
FIG. 6 illustrates an exemplary worksheet for assessing processing speed and executive control in accordance with the present invention.

In step 460, a processing speed and executive control assessment is administered to the participant. In an exemplary implementation, multiple images are presented to the participant simultaneously, for example on a worksheet as shown in FIG. 6 or on a touch screen computing device and the participant is instructed to "mark" as many of the images as they can, and may further be instructed to mark images in a specific order, for example marking all of the bananas shown in FIG. 6 before marking the monkey shown in FIG. 6. Marking may include stamping or otherwise marking an image or, in when a touch screen computing device is used, marking may occur by touching an image to electronically mark the image. The participant's time is recorded when all images are marked. Scoring is based on the number of correct markings, the number of out of range markings, response times, and perseverative responses (multiple markings on same image). This process may be repeated multiple times.

Figure 7:
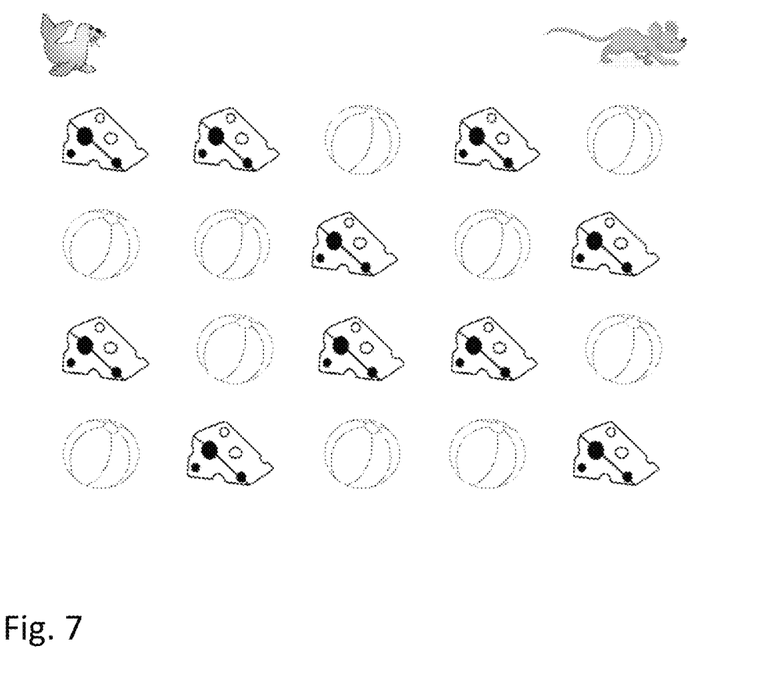
FIG. 7 illustrates an exemplary worksheet for assessing processing speed and executive control in accordance with the present invention.

An inhibition phase may also be tested, where multiple images are administered to the participant simultaneously, and the participant is tasked with marking only specific images (for example, if the images presented are beach balls and cheese, the user is tasked with marking cheese). An exemplary worksheet for administering the inhibition phase is illustrated in FIG. 7. The inhibition phase is preferably discontinued after 1 minute if the participant is not finished, and scoring is based on the number of correct stamps, out of range stamps, and perseverative responses.

A switch phase may also be tested. The switch phase uses an identical image presentation to that of the inhibition phase, as shown in FIG. 7, but the participant is tasked with marking the image not stamped in the inhibition phase (in this case, the participant is tasked with marking beach balls). The switch phase is also preferably discontinued after 1 minute if the participant is not finished. Scoring is based on correct stamps, out of range stamps, perseverative responses, response time, inhibition errors (stamping the wrong image) and self corrections.

If 6 or fewer errors occur in the switch phase, an alternating phase may be administered. For example, if multiple images of beach balls and cheese are displayed, the participant is instructed to alternate between marking cheese and marking beach balls. This is discontinued after 1 minute if the participant does not complete the task before then. Scoring is based on the number of correct markings, the number of out of range markings, the response time, perseverative responses, switch errors, and self-corrections.

In step 465, a spatial short term memory assessment is administered to the participant. In an exemplary implementation, the hiding board and a figurine are used to administer this assessment. The test administrator moves the figurine from one position on the hiding board to a second position to a third position, etc. The participant is then asked to recreate the path taken by the figurine. This process may be repeated multiple times. Scoring is based on correctly re-creating the path of the figurine. Preferably, the assessment is discontinued if the participant fails to recreate the path twice.

In step 470, a story recall assessment is administered to the participant. In an exemplary implementation, the short story recall assessment is based on the story presented in the story memory assessment in step 410. Scoring is awarded based on verbatim recall of specific words, and intrusions or variations are recorded.

In step 472, a delayed visual recognition assessment is administered to the participant. In an exemplary implementation, the participant is shown groups of related images, either via printed images or via a computing device, and the participant is asked to identify the object shown in the images. Preferably, these should be the same items used in step 415. For example, if three different rings are shown to the participant, the participant should identify the images as "ring." Scoring is based on correct responses. Identifying an object by one or more related words is counted as an intrusion.

In step 474, a delayed recall list assessment is administered to the participant. In an exemplary implementation, all items are removed from the participant's view, and the participant is asked to identify all of the objects seen in step 415. Scoring is based on the correct identification of objects presented in step 415.

In step 476, a delayed verbal recognition assessment is administered to the participant. In an exemplary implementation, three words are spoken to the participant ("Did you see X, Y, or Z?"). The participant is asked to identify which of the words was presented as an object in step 415. This is repeated for each object presented in step 415. Scoring is based on correct identification of the objects previously presented.

In step 478, a source memory assessment is administered to the participant. In an exemplary implementation, a plurality of objects is presented to the participant. Some of the objects are new to the user, others have previously been seen in the comprehensive assessment. The participant is then asked to identify the objects that were previously placed on the hiding board. Scoring is based on correct identification of whether or not the object previously appeared on the hiding board.

In step 480, a delayed spatial position recall assessment is administered to the participant. In an exemplary implementation, the hiding board and a plurality of objects (such as jacks) are used to administer this assessment. The plurality of objects may be identical, have the same size and shape, or may be unique. The participant is handed the plurality of objects, and tasked with placing the objects in their previous positions on the hiding board. Scoring is based on the correct placement of the plurality of objects.

In step 482, a delayed scene memory assessment is administered to the participant. In an exemplary implementation, groups of multiple scenes are presented to the participant, either via worksheet or booklet, or via a computing device, and the participant is asked to identify which scene of the group of scenes was seen previously (in step 445). Scoring is based on correct identification of those scenes previously presented.

In step 484, a delayed item in context recall assessment is administered to the participant. In an exemplary implementation, the hiding board, context, and the same objects from the item context assessment of step 455 are presented to the participant, and the participant is asked to recreate each of the hiding boards from step 455. Scoring is based on correct placement of items.

In step 486, a verbal short term memory assessment is administered to the participant. In an exemplary implementation, a plurality of three dimensional objects are placed in front of the participant. The test administrator then asks for specific objects, and the participant is instructed to hand the objects to the test administrator. If trials are repeated, the order of the objects should be scrambled. If the participant fails to correctly identify objects repeatedly, the assessment should be discontinued. If the participant correctly identifies objects, the test administrator may then request a series of objects. Scoring is based on the correct identification of objects in the correct sequence.

In step 488, a verbal fluency assessment is administered to the participant. In an exemplary implementation, the participant is asked to name as many items as possible in a specific category, and the response is timed. For example, the participant may be asked to name as many animals as he or she can think of. Scoring is based on the number of unique responses provided by the participant.

In step 490, a recall composite assessment is administered to the participant. In an exemplary implementation, the participant is asked several questions including, for example, the test administrator's name, where the participant lives, etc. Scoring is based on correct responses.

In step 492, prospective memory recall is assessed. In an exemplary implementation, the participant is asked to recall information about the item(s) introduced in step 405. Scoring is based on correct identification of the items or information from step 405.

Figure 5:
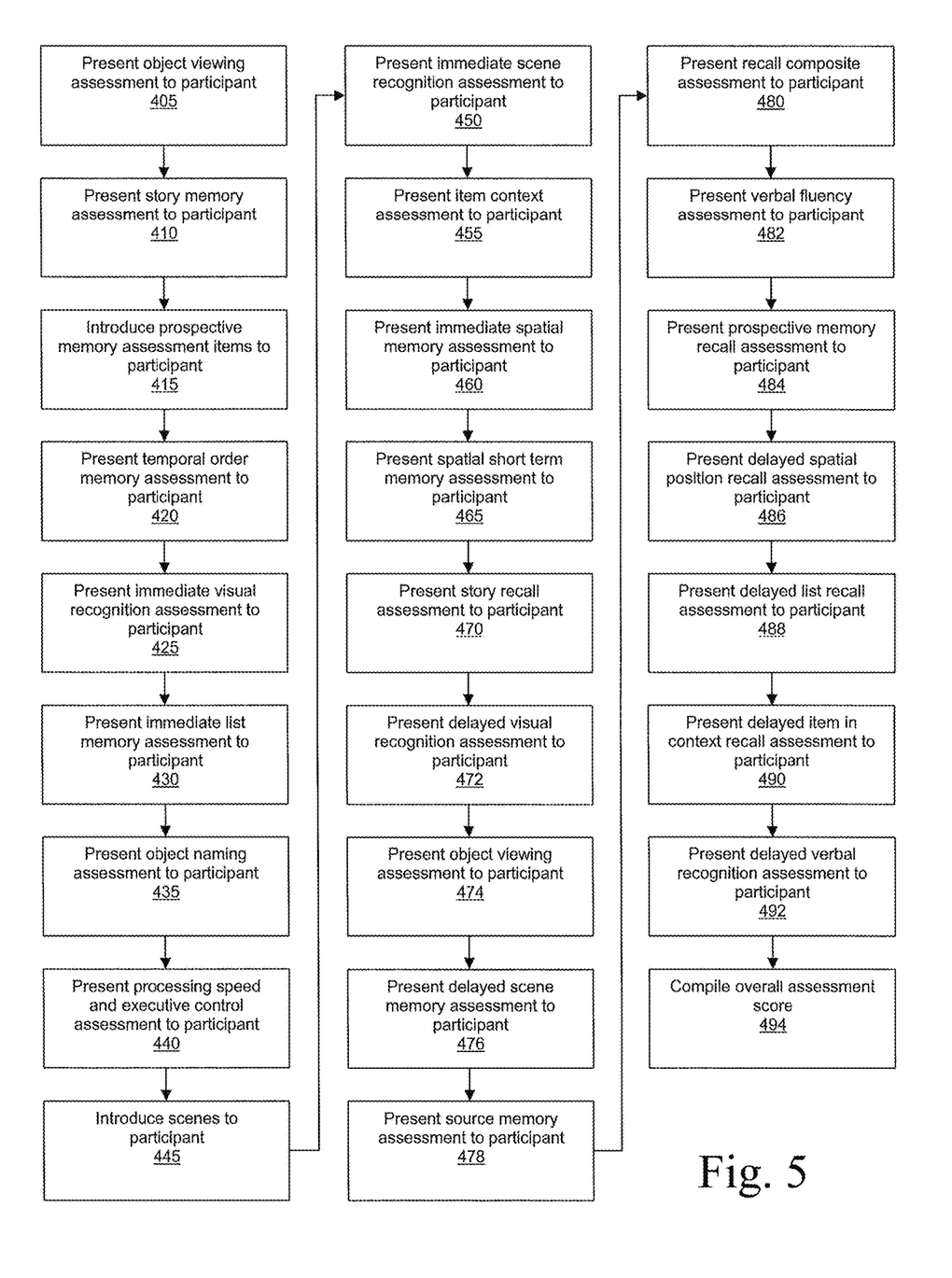
FIG. 5 illustrates an exemplary comprehensive assessment method in accordance with the present invention.

Finally, in step 494, the comprehensive assessment is scored. It should be appreciated that while an exemplary comprehensive assessment is described herein, the various individual assessments that make up the comprehensive assessment can be administered in any order or sequence, so long as the order or sequence permits the introduction of stimuli prior to the individual assessments that rely upon recall or memory of earlier introduced stimuli. For example, the story recall assessment (step 470), delayed visual recognition assessment (step 472), delayed recall list assessment (step 474), delayed visual recognition assessment (step 476), source memory assessment (step 478), delayed spatial position recall assessment (step 480), delayed scene memory assessment (step 482), delayed item in context recall assessment (step 484), and prospective memory recall assessment (step 492) may be administered in any sequence and at any time after the stimuli on which the various individual assessments rely are introduced to the participant. A second exemplary comprehensive assessment is presented in FIG. 5.

While the exemplary implementations described herein with respect to using a physical stimulus booklet, scene cards, and/or worksheet(s) it should be noted that the booklets/worksheets are not limited to physical stimuli and may instead be presented electronically, for example, using a computing device desktop or laptop computer, a tablet computing device, smartphone or the like. Exemplary, non-limiting computer implementations are provided with respect to FIG. 8, which illustrates a computing device in an exemplary form for implementing instructions to execute one or more aspects of the various memory assessments described herein.

Figure 8:
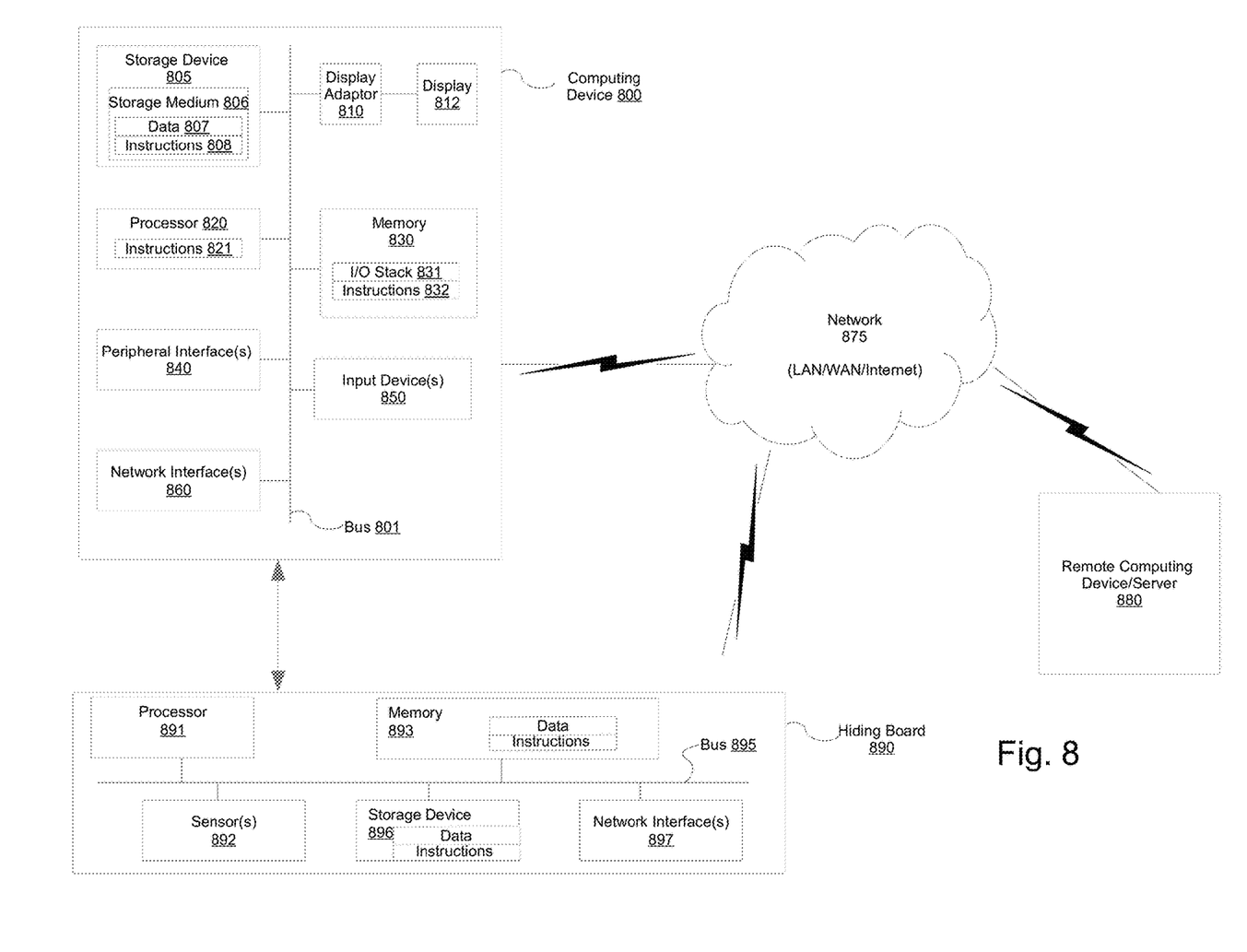
FIG. 8 illustrates an exemplary implementation of a system for computerized implementation of the assessment.

In some implementations, images and/or representations of three-dimensional objects may be presented via computing device 800. Computing device 800 may be any computing device such as a desktop computer, laptop computer, tablet computer (iPad, Android tablet), smartphone, or the like. Computing device 800 may include bus 801 connecting any combination of the following: a storage device 805, a display adapter 810, a display 812, a processor 820, memory 820, peripheral interface(s) 840, input device(s) 850, and network interface(s) 860. Bus 801 may be any known bus structure including, but not limited to, a local bus, memory bus, local controller, memory controller, peripheral bus, bus controller, bus network, etc. or any combination thereof.

Storage device 805 may be any computer-readable storage medium, for example, a hard disk drive, solid state memory, magnetic disk drive, optical disc drive, hybrid drive, or the like. Storage device 805 stores instructions for execution by processor 820 (software), and may also store data. Storage device 805 may be a removable storage medium. Memory 830 may be, for example, any random access memory and may store one or more computer readable instructions embodying any of the various methods described herein. These instructions may be executed by processor 820.

Display adapter 810 communicates an image for display to a user to a display device 812. Display device 812 may be, for example a cathode ray tube display, an LED, LCD, or Plasma display, or a projector for projecting an image onto a flat surface. In some implementations, display device 812 may also incorporate a touch screen such as a capacitive touch screen (for example, as in a smartphone or tablet computing device) or a pressure sensitive touch screen serving as an input device 850. Input device 850, however, may also be a mouse, trackball, stylus, drawing tool, or any other input device.

Network interface 860 may be, for example, a wireless network card operating, for example, on any of the various 802.11 wireless protocols; a Bluetooth adapter; a wired network card connectable to a network via an Ethernet or other wired network protocol, or the like. Network interface 860 allows computing device 800 to communicate with network 875 which may be, for example, a LAN, WAN, connection to the Internet, VPN tunnel, or other connection which ultimately allows for communication with one or more remote computing/server devices. In an implementation, this network connectability would allow for transmission of test instructions and information to computing device 800, and also allow for computing device 800 to transmit data to other computers, for example, a remote data repository for collecting and processing all collected data.

A variety of peripherals may be connected to computer 400 via peripheral interface(s) 840 via, for example, serial or parallel connection, USB connection, Bluetooth connection or the like. In one implementation, electronic hiding board 890 includes an interface 897 to connect and communicate with computing device 800. Electronic hiding board 890 may include a memory 893, such as any storage medium including RAM, for storing instructions; and a processor 891 for executing instructions. A variety of sensors 892 allow for the board to gather data regarding the movement and spatial arrangement of three-dimensional items arranged on the electronic hiding board, and then store that data in storage 896 (hard drive, solid state storage, etc.) until the data can be communicated to computing device 800 via interface 897. In some implementations, the flat surface of the electronic hiding board is formed using the screen of a display device, computing device 800 provides instructions to electronic hiding board 890 to alter the appearance of the display device. In other implementations, the flat surface of electronic hiding board 890 is formed by the screen of a capacitive touch display device (for example, a tablet computing device), and computer 800 may provide instructions to electronic hiding board 890 to highlight specific areas around objects placed on the electronic hiding board 890, for example, in a specific sequence. In still other implementations, electronic hiding board may also store and execute instructions for scoring and interpreting the data collected.

In one implementation, any of the "images" which are described in the examples herein as being presented via scene card, stimulus booklet, or worksheet, may be stored as digital images (JPG, GIF) or as a portable document format in, for example, storage device 405 and displayed to the participant via display 812. In some implementations, computer 400 also stores software that presents each of the images and, when multiple images are presented, allows for the participant to select a specific image by touching the image (using, for example, a capacitive touch screen). In some implementations, selecting the image by touching the image will cause the display of the image to change, for example, indicating that the image is "marked" as in the executive function assessment described herein. In some implementations, computing device 800 is programmed with instructions that allow for scoring of the assessment by the computing device.

The instructions may be stored and executed as part of a special purpose computer application (such as an "app") and may also further serve to automate one or more aspects of one or more memory assessments, for example, by presenting images to a user at pre-defined intervals, providing audio or video instructions and prompts to the user, and/or providing audio, video, or written instructions. Further, the computer program may be used to gather data based on a participants responses received via an input device or peripheral device (electronic hiding board) and recorded by the computer application and stored in computing device 800.

The methods described herein provide for the assessment of a variety of different aspects of memory and learning. Each of the methods for memory assessment described herein may be used individually, in combination with one or more of the other methods for memory assessment described herein. Further, any of the methods described herein may be combined with known methods for memory assessment. The comprehensive memory assessment described herein includes all of the methods for memory assessment described herein as well as known methods for memory assessment. While the memory assessment methods presented herein are described with respect to specific examples, it should be appreciated that deviations from the examples provided herein may be made to accommodate varying levels of attention, language, and motor proficiency or to make the assessment more appropriate for a particular language or cultural group without departing from the scope of the invention. Further, in some implementations, the order of the various memory assessments may be varied without departing from the scope of the invention.

The results of the memory assessments described herein have a variety of implications. For an individual participant, memory performance can be assessed and tracked to determine whether a child is performing at a developmental level appropriate for his/her age group, to gauge the extent of developmental delay and to determine whether improvement occurs over time. To minimize participant familiarity with and practice effects from multiple exposures to the test materials, multiple forms or versions of the various assessments described herein are may be administered over time, with varying stimuli. Results of an individual participant's assessment provide valuable information about the most effective way to present information to that individual so that the information is meaningful to and retained by the individual. This can enhance learning and improve the quality of life for an individual with cognitive impairment. For example, it may provide information to therapists and caregivers about memory and learning abilities that are not often formally assessed because of the lack of appropriate measures.

As previously mentioned, the results of a memory assessment such as this can also provide information as to whether a treatment plan—whether educational early intervention, pharmacological, occupational therapy, surgical treatment, etc.—is working for an individual. This assists in the tailoring of treatment plans to the needs of the individual. By administering the assessment to a broad population with known characteristics, statistical analysis techniques can be used to correlate numeric scores of the memory assessment described herein to qualitative classifications or descriptions, including degrees of cognitive/memory impairment and classifications based on different types of impairments.

What is claimed is:

1. A method for neuropsychological assessment, the method comprising:
    presenting one or more unique three-dimensional objects to a participant in a first arrangement on a hiding board, said hiding board having a flat surface and configured to receive a plurality of three dimensional objects at fixed locations arranged in a nonlinear, non-symmetric, randomly spaced array;
    removing the one or more three-dimensional objects from the hiding board;

re-presenting the one or more three-dimensional objects to the participant in an arrangement that is different from the first arrangement;
instructing the participant to recreate the first arrangement of three-dimensional objects;
receiving a re-created arrangement from the participant that is a re-creation of the first arrangement of three-dimensional objects,
wherein presenting one or more three-dimensional objects to the participant on the hiding board comprises moving a three-dimensional object through a series of positions on the hiding board, and re-creation of the first arrangement comprises moving the one or more three-dimensional objects through the series of positions on the hiding board in sequential order; and
generating an assessment of the participant's memory based on the participant's re-creation of the spatial and temporal components of the first arrangement.

2. The method according to claim 1, further comprising scoring the assessment by awarding points for accurate recreation of the arrangement of each three-dimensional object presented.

3. The method according to claim 1, wherein the first arrangement on the hiding board is a random arrangement of the plurality of three-dimensional objects on the hiding board.

4. The method according to claim 3, wherein the plurality of three-dimensional objects are of the same size.

5. The method according to claim 3, further comprising:
removing the plurality of three-dimensional objects from the hiding board after the first arrangement has been recreated;
receiving a re-creation of a second arrangement from the participant after a period of time has elapsed, said second arrangement being a re-creation of the first arrangement by the participant a second time after a period of time has elapsed: and
generating a further assessment of the participant's memory.

6. The method according to claim 1, further comprising:
presenting a second plurality of three-dimensional objects to the participant, the second plurality of three-dimensional objects including at least one three-dimensional object previously presented to the participant on the hiding board;
identifying by the participant which of the second plurality of three-dimensional objects was previously presented on the hiding board; and
generating a further assessment of the participant's memory.

7. The method according to claim 1, wherein the first arrangement further comprises presenting the plurality of three-dimensional objects in a first context.

8. The method according to claim 7, further comprising:
presenting the one or more three-dimensional objects to the participant in a second arrangement on the hiding board;
removing the one or more three-dimensional objects from the hiding board;
re-present the one or more three-dimensional objects to the participant in an arrangement that is different from the first arrangement or the second arrangement;
receiving an arrangement from the participant that is a re-creation of the second arrangement; and
generating a further assessment of the participant's memory.

9. The method according to claim 8, wherein presenting the one or more three-dimensional objects to the participant in a second arrangement further comprises presenting the one or more three-dimensional objects to the participant in a second context.

* * * * *